(12) United States Patent
Schlama et al.

(10) Patent No.: US 6,596,905 B1
(45) Date of Patent: Jul. 22, 2003

(54) METHOD FOR PREPARING AROMATIC DIPHENYL THIOETHERS

(75) Inventors: Thierry Schlama, Dardilly (FR); Jean-Christophe Bigouraux, Dargoire (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/868,823

(22) PCT Filed: Dec. 23, 1999

(86) PCT No.: PCT/FR99/03273

§ 371 (c)(1), (2), (4) Date: Aug. 27, 2001

(87) PCT Pub. No.: WO00/39079

PCT Pub. Date: Jul. 6, 2000

(30) Foreign Application Priority Data

Dec. 23, 1998 (FR) .............................................. 98 16372

(51) Int. Cl.⁷ ............................................ C07C 319/00
(52) U.S. Cl. ............................. 568/56; 568/58; 546/294
(58) Field of Search ............................... 568/38, 39, 41, 568/42, 44, 47, 56, 58; 546/290, 294

(56) References Cited

U.S. PATENT DOCUMENTS 4,542,233 A * 9/1985 Piccolo et al. .............. 558/376
4,686,303 A * 8/1987 Bauer et al. ................. 560/18

OTHER PUBLICATIONS

A. Arcoria, et al.: Gazzetta Chimica Italiana, vol. 91, 1961, pp. 223–241, XP002112733.

U. Schmidt, et al. : Liebigs Annalen Der Chemie, vol. 672, 1964, pp. 78–90, XP002112732 Verlag Chemie, Weinheim, DE.

A. Mangini et al. "Su alcuni aril–sulfoni" Bolletino Scientifico Della Facolta Di Chimica Industriale Di Bologna, vol. 14, 1956, pp. 81–95, XP002112734.

G. Leandri et al.; Annali Di Chimica, vol. 46, 1956, pp. 1069–1079, XP002112735.

* cited by examiner

Primary Examiner—Jean F. Vollano

(57) ABSTRACT

The invention concerns a method for preparing aromatic diphenyl thioethers. More particularly the invention concerns the preparation of 4-chloro-4'-thiomethyldiphenylether. The inventive method for preparing an aromatic diphenyl thioether is characterised in that it consists in reacting in an aqueous medium a diazonium salt of an aromatic diphenyl compound with a disulphide sulphur compound, in the presence of an efficient amount of a coupling catalyst.

40 Claims, No Drawings

METHOD FOR PREPARING AROMATIC DIPHENYL THIOETHERS

This application is an application under 35 U.S.C. Section 371 of International Application Number PCT/FR99/03273 filed on Dec. 23, 1999.

The present invention relates to a process for preparing biphenyl type aromatic thioethers.

More precisely, the invention relates to the preparation of an aromatic compound comprising a concatenation of at least two phenyl groups at least one of which carries a thioether group.

More particularly, the invention relates to the preparation of 4-chloro-4'-thiomethyldiphenyether.

When a functional group is to be introduced into a biphenyl type molecule, there is a problem with introducing a functional group into only one of the benzene rings.

The present invention aims to provide a process that consists of introducing at least one thioether group into one of the phenyl groups.

It has now been discovered, and this forms the subject matter of the present invention, a process for preparing a biphenyl type aromatic thioether, characterized in that a diazonium salt of a biphenyl type aromatic compound is reacted with a disulphide type sulphur-containing compound in an aqueous medium in the presence of an effective quantity of a coupling catalyst.

The term "biphenyl type aromatic thioether" means a concatenation of two phenyl groups connected together wherein at least one of the benzene rings carries a thioether function.

In a preferred variation of the process of the invention, the thioether is prepared using a process that associates preparation of the diazonium salt from the corresponding aromatic amine then, without separation, carrying out the reaction with the sulphur-containing compound.

In accordance with the process of the invention, a biphenyl type aromatic amine can be used as the starting compound; in a first step, it is transformed into a diazonium salt.

The term "biphenyl type aromatic amine" means a concatenation of two phenyl groups connected together wherein at least one of the benzene rings carries an amine function.

The starting aromatic amine can be represented by the following general formula (1):

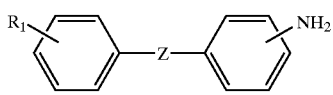
(I)

in which formula (I):

$R_1$ represents a hydrogen atom or a substituent R;

Z represents:
  a covalent bond;
  an alkylene or alkylidene group containing 1 to 4 carbon atoms, preferably a methylene or isopropylidene group;
  a group B which may be one of the following atoms or groups:

—O—, —CO—, —COO—, —OCOO—
—S—, —SO—, —SO$_2$—,

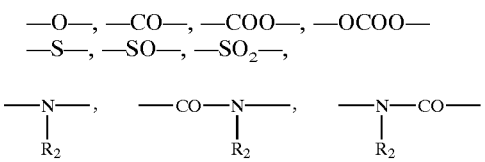

in which formulae, $R_2$ represents a hydrogen atom or an alkyl group containing 1 to 6 carbon atoms, or a phenyl group.

In formula (I), one or both benzene rings can be substituted, meaning that in the biphenyl type starting substrate, at least one of the 5 hydrogen atoms of the aromatic ring can be replaced by an atom other than a hydrogen atom. In particular, it can be a halogen atom, carbon, oxygen or nitrogen.

Group $R_1$ represents a hydrogen atom or any other group R.

Group R can have any nature provided that it does not interfere with the diazotisation reaction.

Non-limiting examples of substituents that can be cited are given below:
  a linear or branched alkyl group, preferably containing 1 to 6 carbon atoms, more preferably 1 to 4 carbon atoms;
  a linear or branched alkenyl group preferably containing 2 to 6 carbon atoms, more preferably 2 to 4 carbon atoms;
  a linear or branched halogenoalkyl group preferably containing 1 to 4 carbon atoms, and 1 to 9 halogen atoms;
  a cycloalkyl group containing 3 to 7 carbon atoms, preferably a cyclohexyl group;
  a phenyl group;
  a hydroxyl group;
  a NO$_2$ group;
  a $R_3$—O— alkoxy group or $R_3$—S— thioether group where $R_3$ represents a linear or branched alkyl group containing 1 to 6 carbon atoms, preferably 1 to 4 carbon atoms, or a phenyl group;
  a —N—(R$_2$)$_2$ group where groups $R_2$, which may be identical or different, represent a hydrogen atom, a linear or branched alkyl group containing 1 to 6 carbon atoms, preferably 1 to 4 carbon atoms, or a phenyl group;
  a —NH—CO—R$_2$ group where $R_2$ has the meaning given above;
  a carboxyl group or R$_2$—O—CO— derivative, where group $R_2$ has the meaning given above;
  an acyloxy or aroyloxy group $R_3$—CO—O—, where group $R_3$ has the meaning given above;
  a B(OR$_3$)$_2$ group, where group $R_3$ has the meaning given above;
  a halogen atom, preferably a fluorine atom;
  a CF$_3$ group;
  two groups R can together form an alkylenedioxy group containing 1 to 4 atoms in the alkylene group, preferably a methylenedioxy or ethylenedioxy group.

Preferred groups R that can be cited are a halogen atom, preferably a fluorine, chlorine or bromine atom or a halogenoalkyl group, preferably perfluoroalkyl; a hydroxyl group; an alkyl or alkoxy group containing 1 to 6 carbon atoms, preferably 1 to 4 carbon atoms; an amino group or an amino group substituted with one or two alkyl groups containing 1 to 6 carbon atoms, preferably 1 to 4 carbon atoms.

Preferred compounds are those with formula (I) where $R_1$ represents a fluorine atom or a chlorine atom and Z represents an oxygen atom.

In accordance with the process of the invention, in a first step the diazonium salt of the biphenyl type aromatic amine preferably with formula (I) is prepared.

To this end, to transform the amino group into a diazonium group, the starting substrate is reacted with an acid. While it is possible to use an acid such as sulphuric acid, it is preferable to use a hydrogen acid to put the amine group into the halohydrate salt form.

Thus, the starting substrate preferably with formula (I) is preferably reacted with hydrochloric acid or hydrobromic acid.

The quantity of acid used is such that the mole ratio between the number of $H^+$ ions and the number of moles of substrate is in the range 2.0 to 2.5, preferably in the range 2.0 to 2.2.

In the next step, the diazonium salt is prepared by reacting the biphenyl type aromatic amine in the halohydrate form with a diazotisation reactant that is any source of NO+.

Thus it is possible to start from nitrogen dioxide $NO_2$, nitrogen trioxide $N_2O_3$, nitrogen tetroxide $N_2O_4$, nitric oxide NO associated with an oxidising agent such as nitric acid, nitrogen dioxide or oxygen. When the reactant is a gas under the reaction conditions, it is bubbled into the mediun.

It is also possible to use a nitrous acid, a nitrosyl sulphide or a nitrose or a nitrous salt, preferably an alkali metal salt, more preferably a sodium salt.

It is also possible to use alkyl nitrites, more particularly those with formula (II):

$$R_a\text{—ONO} \qquad (II)$$

in which formula (II), $R_a$ represents a linear or branched alkyl group containing 1 to 12 carbon atoms, preferably 1 to 4 carbon atoms.

Advantageously, sodium nitrite is used.

The quantity of diazotisation reactant used can vary widely. When it is expressed as the mole ratio of the aromatic aminel diazotisation reactant defined as $NO^+$, it is at least equal to the stoichiometric quantity but preferably, it is used in an excess of up to 120% of the stoichiometric quantity, preferably in the range 100% to 120%.

Regarding the concentration of the aromatic amine substrate in the reaction medium, it is preferably in the range 0.5 to 2.5 mol/l, more preferably about 1 mol/l.

The amine halohydrate is prepared by simply mixing the starting amine and the acid.

The reaction is advantageously carried out at a temperature in the range 50° C. to 100° C.

The diazotisation reactant is then added, preferably slowly in fractions or continuously.

Regarding the temperature of the diazotisation reaction, this is generally a low temperature, advantageously in the range −10° C. to 20° C., preferably in the range 0° C. to 10° C.

In the process of the invention, the sulphur-containing compound is reacted with the diazonium salt obtained, which preferably has the following formula (III):

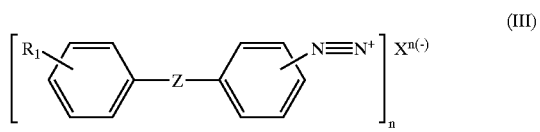

in which formula (III):
X represents a halogen atom X, preferably a chlorine or bromine atom, a $HSO_4^-$ group or a $SO_4^=$ group;
$R_1$ and Z have the meanings given above;
n equals 1 or 2.

The sulphur-containing compound used preferably has the following formula (IV):

$$R_4\text{—S—S—}R_5 \qquad (IV)$$

in said formula (IV):
$R_4$ and $R_5$, which may be identical or different, represent a hydrocarbon group containing 1 to 24 carbon atoms, which can be a saturated or unsaturated, linear or branched aliphatic acyclic group; a saturated, unsaturated or aromatic, monocyclic or polycyclic carbocyclic or heterocyclic group, or a linear or branched, saturated or unsaturated aliphatic group carrying a cyclic substituent.

The sulphur-containing compound used in the process of the invention has formula (IV) where $R_4$ and $R_5$ can have a number of meanings. Different, non-limiting, examples will be given below.

With compounds with formula (IV), $R_4$ and $R_5$ preferably represent a saturated or unsaturated, linear or branched acyclic aliphatic group preferably containing 1 to 24 carbon atoms, comprising one or more unsaturated bonds in the chain, generally 1 to 3 unsaturated bonds which may be simple double bonds or conjugated double bonds or triple bonds.

More particularly, $R_4$ and $R_5$ represent a linear or branched alkyl, alkenyl, or alkadienyl group preferably containing 1 to 12 carbon atoms.

$R_4$ and $R_5$ represent a linear or branched halogenoalkyl group preferably containing 1 to 12 carbon atoms, more preferably 1 to 4 carbon atoms, and 3 to 25 halogen atoms.

The hydrocarbon chain can optionally be:
interrupted by a functional atom or group; groups B cited above may be cited in this respect;
and/or carry the following substituents:
—OH, —$COR_3$, —$COOR_2$, —CHO, —CN, —$NO_2$, —$CF_3$,
where $R_2$, which may be identical or different, and $R_3$ have the meaning given above.

Groups $R_4$ and $R_5$ can represent a halogenoalkyl group, preferably perhalogenoalkyl, or a halogenoalkenyl group.

In formula (IV), the saturated or unsaturated linear or branched aliphatic acyclic group can optionally carry a cyclic substituent. The term "cycle" means a saturated, unsaturated or aromatic carbocyclic or heterocyclic cycle.

The aliphatic acyclic group can be bonded to the cycle by a covalent bond or by a group B as cited above.

Examples of cyclic substituents that can be envisaged are cycloaliphatic, aromatic or heterocyclic substituents, in particular cycloaliphatic substituents containing 6 carbon atoms in the cycle or benzenic substituents, such cyclic substituents themselves optionally carrying one or more substituents.

Examples of such groups that can be mentioned are the benzyl group.

In general formula (IV), $R_4$ and $R_5$ can represent a monocyclic carbocyclic group. The number of carbon atoms in the cycle can vary widely from 3 to 8 carbon atoms, but is preferably 5 or 6 carbon atoms.

The carbocyle can be saturated or may comprise 1 or 2 unsaturated bonds in the cycle, preferably 1 or 2 double bonds.

Preferred examples of groups $R_4$ and $R_5$ that can be cited are cyclohexyl or cyclohexeneyl groups.

When $R_4$ or $R_5$ represents a saturated or unsaturated monocyclic carbocyclic group, one or more of the carbon atoms of the cycle may be replaced by a heteroatom, preferably oxygen, nitrogen or sulphur or by a fimctional group, preferably carbonyl or ester, leading to a monocyclic heterocyclic compound. The number of atoms in the cycle can be in the range 3 to 8 atoms, preferably 5 or 6 atoms.

Groups $R_4$ and $R_5$ can also be polycyclic carbocyclic, preferably bicyclic, meaning that at least two cycles have two carbon atoms in common. With polycyclic groups, the number of carbon atoms in each cycle is in the range 3 to 6: the total number of carbon atoms is preferably 7.

Groups $R_4$ and $R_5$ can also be polycyclic heterocyclic, preferably bicyclic, which means that at least two cycles have two atoms in common. In this case, the number of atoms in each cycle is in the range 3 to 6, more preferably 5 or 6.

Groups $R_4$ and $R_5$ preferably represent an aromatic carbocyclic group, in particular benzenic or a concatenation of 2 or 3 benzene rings separated by atoms or groups B as defined above.

Examples of groups $R_4$ and $R_5$ with formula (IV) that can more particularly be mentioned are phenyl groups.

$R_4$ and $R_5$ can also represent a polycyclic aromatic hydrocarbon group; the cycles can between them form ortho-condensed or ortho- and peri-condensed systems. More particularly, the group can be the naphthyl group.

In general formula (IV), $R_4$ and $R_5$ can also represent an aromatic heterocyclic group in particular comprising 5 or 6 atoms in the cycle, wherein 1 or 2 are heteroatoms such as nitrogen, sulphur or oxygen.

Illustrative examples of heterocyclic groups that can be cited are tetrahydrofuryl, tetrahydrothienyl, pyrrolidinyl, furyl, thienyl, pyrrolyl and pyridyl.

$R_4$ and $R_5$ can also represent a polycyclic aromatic heterocyclic group defined as either a group constituted by at least two aromatic or non aromatic heterocycles containing at least one heteroatom in each cycle and forming between them ortho- or ortho- and peri-condensed systems, or a group constituted by at least one aromatic or non aromatic hydrocarbon cycle and at least one aromatic or non aromatic heterocycle forming between them ortho- or ortho- and peri-condensed systems.

Illustrative examples of polycylic groups that can be cited are: isoquinolyl, quinolyl, naphthyridinyl, benzofuranyl and indolyl.

It should be noted that if group $R_4$ and $R_5$ comprises a cycle, that cycle may carry a substituent. The nature of the substituent is irrelevant as long as it does not interfere with the desired product. The substituents are of the same nature as R.

Preferred examples of groups $R_4$, $R_5$ that can be cited are linear or branched alkyl groups containing 1 to 4 carbon atoms, 2-carboxyethyl, cyclohexyl, phenyl, benzyl, benzoyl, pyridyl, etc.

The process is readily carried out using a number of sulphur-containing compounds.

Preferred examples of disulphide type sulphur-containing compounds that can be mentioned are:

dimethyldisulphide;
diethyldisulphide;
di-n-propyldisulphide;
diisopropyldisulphide;
di-n-butyldisulphide;
diisobutyldisulphide;
di-sec-butyldisulphide;
di-tert-butyldisulphide;
diisoamyldisulphide;
di-n-hexyldisulphide;
di-tert-heptyldisulphide;
di-n-undecyldisulphide;
distearyldisulphide;
diallyldisulphide;
dicyclohexyldisulphide;
diphenyldisulphide;
dibenzyldisulphide
dibenzoyldisulphide;
dithiopyridine;
dithioglycolic acid.

Preferred compounds from the list cited above are dialkyldisulphides preferably containing 1 to 4 carbon atoms in the alkyl portion.

The quantity of sulphur-containing compound is such that said mole ratio is preferably in the range 1 to 1.5.

The coupling reaction is carried out in an aqueous medium. The quantity of water present in the reaction medium generally represents 100% to 500% by weight of the aromatic amine.

In a variation, the process of the invention consists of adding an organic solvent which is inert under the reaction conditions.

Examples of organic solvents that can be cited are saturated aliphatic monocarboxylic acids, more particularly formic acid, acetic acid, propionic acid, butyric acid, isobutyric acid, pentanoic acid and 2-methylbutanoic acid.

Acetic acid is the preferred saturated aliphatic monocarboxylic acid.

It is also possible to use a solvent such as acetone or dimethylformamide.

The quantity of organic solvent used, expressed as the weight of starting amine, is advantageously in the range 100% to 1000%, preferably in the range 200% to 500%.

In the process of the invention, the diazonium salt, preferably with formula (III), is reacted with the sulphur-containing compound, preferably with formula (IV): the reaction is carried out in the presence of a coupling catalyst.

The coupling catalyst is a catalyst comprising at least one metallic element selected from the $4^{th}$ and $5^{th}$ period of groups IIIA, IVA, VA, VIA, VIIA, VIII, IB and IIB of the periodic table.

Preferred metals that can be cited are: copper, iron, cobalt, nickel, palladium and platinum.

The elements are defined in the periodic table published in the "Bulletin de la SociétéChimique de France, No.1 (1966).

The metallic elements can also be supplied in the form of a zero metal or an inorganic derivative such as an oxide or hydroxide. It is possible to use a mineral salt, preferably a nitrate, sulphate, oxysulphate, halide, oxyhalide, silicate, carbonate or an organic derivative, preferably a cyanide, oxalate, acetylacetonate; an alcoholate, more preferably a methylate or ethylate; or a carboxylate, more preferably an acetate. It is also possible to use complexes, in particular chlorine-containing or cyanide-containing complexes of said metals and/or alkali metals, preferably sodium or potassium, or ammonium.

More specific examples of palladium catalysts that can be cited are palladium (II) chloride, hydrated palladium (II) nitrate, dihydrated palladium (II) sulphate, palladium (II) acetate, ammonium tetrachloropalladate (II), potassium hexachloropalladate (IV), and palladium (II) tetrakisphenylphosphine.

Platinum catalysts that can be mentioned include platinum (II) chloride, ammonium tetrachlorplatinate (II), ammonium hexachloroplatinate (IV), hydrated sodium tetrachloroplatinate (IV), hexahydrated sodium hexachloroplatinate (IV), potassium hexachloroplatinate (IV), and hexahydrated chloroplatinic acid.

Nickel or cobalt catalysts that can be cited include nickel (II) bromide and chloride and cobalt (II) chloride or bromide.

The catalyst of choice used in the process of the invention is copper-based.

Examples of catalysts that can be cited are copper metal or organic or inorganic copper I or copper II compounds.

Preferably, catalysts based on copper 0 and I are used.

Non limiting examples of copper compounds that can be cited are cuprous bromide, cupric bromide, cuprous iodide, cuprous chloride, cupric chloride, basic copper II carbonate, cuprous nitrate, cupric nitrate, cuprous sulphate, cupric sulphate, cuprous sulphite, cuprous oxide, cuprous acetate, cupric acetate, cupric trifluoromethylsulphonate, cupric hydroxide, copper I methylate, copper II methylate, and chlorocupric methylate with formula $ClCuOCH_3$.

The quantity of catalyst used, expressed as the ratio of the weight of diazonium salt is generally in the range 0.1 to 20 mole %, preferably 1% to 10%.

The coupling reaction between the diazonium salt preferably with formula (III) and the sulphur-containing compound is advantageously carried out at a temperature in the range 0° C. to 120° C., preferably in the range 80° C. to 100° C.

In general, the reaction is carried out at atmospheric pressure, but lower or higher pressures may also be suitable. Autogenous pressure is employed when the reaction temperature is higher than the boiling temperature of the reactants and/or products.

In a preferred variation of the process of the invention, the process of the invention is carried out in a controlled atmosphere of inert gas. A rare gas atmosphere can be established, preferably argon, but nitrogen is more economical.

The reaction is continued until the diazonium salt is completely transformed. The reaction progress can be monitored using any conventional analytical technique such as gas chromatography or high performance liquid chromatography.

The reaction period is generally short, of the order of 30 min to 2 hours.

From a practical viewpoint, the two reactants are brought together in any order. In a preferred variation, the sulphur-containing compound is preferably added to the diazonium salt, followed by the catalyst.

At the end of the reaction, two phases are obtained; the aqueous phase comprises all of the salts formed and the organic phase comprises, in addition to any excess reactants, the desired compound which preferably has formula (VI):

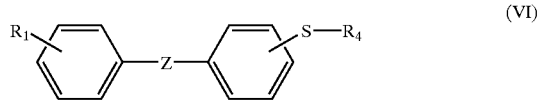

in which formula (VI), $R_1$, $R_4$ and Z have the meanings given above.

The desired product is recovered from the organic phase using conventional techniques. By way of illustration, it is possible to add an organic solvent, for example isopropyl ether or an alkane such as methylcyclohexane, to extract all of the organic compounds and then, from this organic phase, to separate the compound using the usual separation techniques such as distillation or crystallisation from a suitable solvent, preferably an alcohol, more particularly methanol or isopropanol.

The following examples are given by way of illustration and are in no way limiting in nature.

The following abbreviations are used in the examples:

TT=number of moles of 4-chloro-4'aminodiiphenylether transformed,/number of moles of 4-chloro-4'aminodiphenylether introduced%

RR=number of moles of 4-chloro-4'thiomethyldiphenylether formed,/ Number of moles of 4-chloro-4'aminodiphenylether introduced%

EXAMPLE 1

2.20 g (10 mmoles) of 4-chloro-4'-aminodiphenylether, 8 ml of water and, with stirring, 2.33 g (23 mmoles) of 36% hydrochloric acid were charged into a 50 ml double envelope reactor.

It was heated to 90° C. and the mixture became homogeneous.

This temperature was maintained for 45 minutes then it was cooled to 10° C.

0.69 g (10 mmoles) of an aqueous 30% sodium nitrite solution was poured in over two hours using a syringe driver.

The diazonium salt was added dropwise to a mixture of 0.82 g of dimethyldisulphide and 5 ml of water and 31 mg of copper metal in a 100 ml reactor at 50° C.

15 ml of isopropyl ether was added.

The reactor was emptied and the organic phase was washed with 100 ml of water and 100 ml of 10% sodium bisulphite in water and again with 100 ml of water.

The organic phase was concentrated under reduced pressure of 2 mbars, at 50° C. for 1 hour.

1.38 g of 4-chloro4'-thiomethyldiphenylether was obtained, corresponding to a degree of transformation of 100% and a yield RR of 55%.

The product obtained could be purified by crystallisation from methanol.

EXAMPLES 2 TO 14

The above example was repeated, changing the nature of the catalyst.

The quantity of product formed was determined by gas chromatographic analysis.

The results are shown in Table (I).

TABLE (I)

| Ex. Ref | Nature of catalyst | Yield |
|---------|-------------------|-------|
| 2 | $CuBr_2$ | 63.0% |
| 3 | $CuSO_4$ | 62.7% |
| 4 | $CuCl_2,2H_2O$ | 61.2% |
| 5 | CuBr | 48.9% |
| 6 | $Cu_2O$ | 37.3% |
| 7 | $Pd(AcO)_2$ | 26.6% |
| 8 | $Pd(PPh_3)_4$ | 25.5% |
| 9 | $NiBr_2$ | 24.6% |
| 10 | $PdCl_2$ | 24.4% |
| 11 | $CoCl_2,6H_2O$ | 20.2% |
| 12 | Pd/C | 18.9% |
| 13 | $MnCl_2$ | 14.4% |
| 14 | $AgNO_3$ | 10.9% |

EXAMPLE 15

165 g of Cl—Ph—O—Ph—$NH_2$ (0.75 moles) was charged into a 2.0 litre three-necked flask provided with a thermometer, a dropping funnel, a coolant surmounted by an argon reservoir (balloon) and maintained under an inert atmosphere with vigorous magnetic stirring. 300 ml of acetic acid was then added.

The assembly was heated to 80° C. then 82.5 g of a concentrated aqueous hydrochloric acid solution (37%) was slowly added.

The reaction medium was stirred for about 45 min at 80° C.

The temperature was allowed to return to 65° C. with stirring.

213 g of $CuCl_2$ was then added to the reaction medium, followed by 132 ml of $Me_2S_2$.

Then an aqueous $NaNO_2$ solution (solution of 54 g in 120 ml of $H_2O$) was added using the dropping funnel.

When no more gas had been released, the temperature was returned to ambient temperature and the medium was diluted with 360 ml of water. Two phases appeared.

500 ml of methycyclohexane was added and the two phases were separated.

The aqueous phase was extracted again with methylcyclohexane (500 ml).

After evaporating off the methylcyclohexane, 242 g of a brown oil was recovered. The crude product was recrystallised to produce 124 g of pink-white crystals (yield: 66%; purity: 97.2%, determined by gas chromatography; and MPt=56.0° C.).

A second recrystallisation was possible.

What is claimed is:

1. A process for preparing a biphenyl aromatic thioether compound, comprising the step of reacting a diazonium salt of a biphenyl aromatic compound with a disulphide compound, in an aqueous medium, and in the presence of a catalyzing effective amount of a coupling catalyst.

2. A process according to claim 1, comprising the following steps:

1) preparing the diazonium salt from a biphenyl aromatic amine compound, then, without separation, 2) reacting with the diazonium salt with the disulphide compound.

3. A process according to claim 2, wherein the biphenyl aromatic amine compound has the following formula (I)

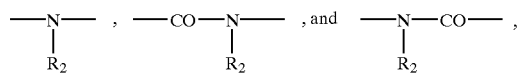

wherein $R_1$ is a hydrogen atom or a substituent R which does not interfere with the diazonium salt reaction, and Z is:

a covalent bond, an alkylene or alkylidene group having 1 to 4 carbon atoms, or a group or atom B selected from the group consisting in the groups or atoms of the following formula:
—O—, —CO—, —COO—, —OOC—, —OCOO—, —S—, —SO—, —$SO_2$—, $$-\underset{R_2}{N}-, \quad -CO-\underset{R_2}{N}-, \text{ and } -\underset{R_2}{N}-CO-,$$

wherein $R_2$ is a hydrogen atom, an alkyl group having 1 to 6 carbon atoms, or a phenyl group.

4. A process according to claim 3, wherein Z a methylene group or an isopropylidene group.

5. A process according to claim 3, wherein R is:

a linear or branched alkyl group, a linear or branched alkenyl group, a linear or branched halogenoalkyl group, a cycloalkyl group having 3 to 7 carbon atoms, a phenyl group, a hydroxyl group, a $NO_2$ group, a $R_3$-O— alkoxy group or a $R_3$—S— thioether group wherein $R_3$ is a linear or branched alkyl group having 1 to 6 carbon atoms, a —N—$(R2)_2$ group wherein $R_2$, which is identical or different, is a hydrogen atom, or a linear or branched alkyl group having 1 to 6 carbon atoms, a —NH—CO—$R_2$ group wherein $R_2$ is a hydrogen atom, or a linear or branched alkyl group having 1 to 6 carbon atoms, a carboxyl group or a $R_2$—O—CO— group, wherein R2 is a hydrogen atom, or a linear or branched alkyl group having 1 to 6 carbon atoms, an acyloxy or aroyloxy group $R_3$—O—O—, wherein $R_3$ is a linear or branched alkyl group having 1 to 6 carbon atoms, a $B(OR_3)_2$ group, wherein $R_3$ is a linear or branched alkyl group having 1 to 6 carbon atoms, or a $CF_3$ group.

6. A process according to claim 5, wherein R is a methylenedioxy group or an ethylenedioxy group.

7. A process according to claim 2, wherein step 1) comprises the preparation of the dfazonium salt of the biphenyl aromatic amine by reacting said amine with a hydrogen acid and a diawotisation source of $NO^+$.

8. A process according to claim 7, wherein the hydrogen acid is hydrochloric acid or hydrobromic acid.

9. A process according to claim 7, the number of $H^+$ ions of the acid and the number of moles of the amine is in a molar ratio in the range from 2.0 to 2.5.

10. A process according to claim 9, wherein the mole ratio is in the range from 2.0 to 2.2.

11. A process according to claim 7, wherein the reaction between the biphenyl aromatic amine and the hydrogen acid is carried out at a temperature in the range from 50° C. to 100° C.

12. A process according to claim 7, wherein the source of $NO^+$ is a $NO$, $NO_2$, $N_2O_3$, $N_2O_4$, associated with an oxidising agent.

13. A process according to claim 3, wherein the diazonium salt has the following formula (III):

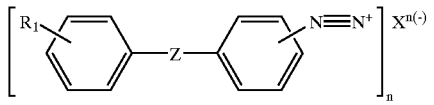

(III)

wherein:

X is a halogen atom, a $HSO_4^-$ group, or a $SO_4^=$ group, n is 1 or 2, $R_1$ is a hydrogen atom or a substituent R which does not interfere with the diazonium salt reaction, and Z is:
a covalent bond,
an alkylene or alkylUdene group containing 1 to 4 carbon atoms, or
a group or atom B selected from the group consing in the groups or atoms of the following formula:
—O—, —CO—, —COO—, —OOC—, —OCOO—,
—S—, —SO—, —SO$_2$—,

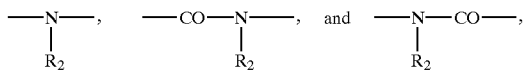

wherein $R_2$ is a hydrogen atom, an alkyl group having 1 to 6 carbon atoms, or a phenyl group.

14. A process according to claim 1, wherein the disulphide compound has the following formula (IV):

$R_4$—S—S—$R_5$ (IV)

wherein $R_4$ and $R_5$, which are identical or different, are hydrocarbon groups having 1 to 24 carbon atoms.

15. A process according to claim 14, wherein $R_4$ and $R_5$, which are identical or different, are saturated or unsaturated, linear or branched, acyclic aliphatic groups.

16. A process according to claim 14, wherein $R_4$ and $R_5$, which are identical or different, are saturated, unsaturated or aromatic, monocyclic or polycyclic, carbocyclic groups.

17. A process according to claim 14, wherein $R_4$ and $R_5$, which are identical or different, are linear or branched, saturated or unsaturated, aliphatic groups beanng a cyclic substituent.

18. A process according to claim 15, wherein $R_4$ and R5 represent 1 to 3 unsaturated bonds, selected from the group consisting of conjugated double bonds, and triple bonds.

19. A process according to claim 14, wherein $R_4$ and $R_5$ are linear alkyl groups, branched alkyl groups, alkenyl groups, or alkyldienyl groups.

20. A process according to claim 19, wherein $R_4$ and $R_5$ present an hydrocarbon chain which:

is interrupted by an atom or a functional group B selected from the group consisting in the groups or atoms of the following formula:

—O—, —CO—, —COO—, —OOC—, —OCOO—,
—S—, —SO—, —SO$_2$—,

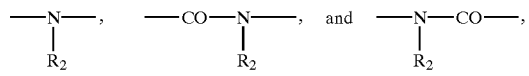

wherein $R_2$ is a hydrogen atom, an alkyl group having 1 to 6 carbon atoms, or a phenyl group, or bears one of the following substituents:
—OH, —COR$_3$, —COOR$_2$, —CHO, —CN, —NO$_2$, —CF$_3$,
wherein $R_2$, which is identical or different, and $R_3$, are hydrogen atoms, alkyl groups having 1 to 6 carbon atoms, or phenyl groups.

21. A process according to claim 14, wherein $R_4$ and $R_5$ are linear or branched halogenoalyl groups having 1 to 12 carbon atoms.

22. A process according to claim 17, wherein $R_4$ and $R_5$ bear a benzene ring.

23. A process according to claim 22, wherein an acyclic aliphatic group is bonded to the benzene ring via a covalent bond or by a group B selected from the group consisting in the groups or atoms of the following formula:

—O—, —CO—, —COO—, —OOC—, —OCOO—,
—S—, —SO—, —SO$_2$—,

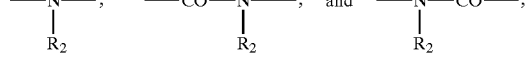

wherein $R_2$ is a hydrogen atom, an alkyl group having 1 to 6 carbon atoms, or a phenyl group.

24. A process according to claim 14, wherein $R_4$ and $R_5$ are:
monocyclic carbocyclic groups, saturated or having 1 or 2 unsaturated bonds in a cycle, the number of carbon atoms in the cycle being in the range frorn 3 to 8, or
polycyclic carbocyclic groups, the number of carbon atoms in a cycle being in the range from 3 to 8.

25. A process according to claim 14, wherein $R_4$ and $R_5$ are benzene rings or a concatenation of 2 or 3 benzene rings separated by atoms or groups B selected from the group consisting in the groups or atoms of the following formula:

—O—, —CO—, —COO—, —OOC—, —OCOO—,
—S—, —SO—, —SO$_2$—,

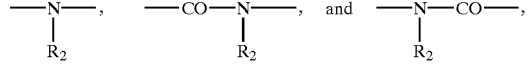

wherein $R_2$ is a hydrogen atom, an alkyl group having 1 to 6 carbon atoms, or a phenyl group.

26. A process according to claim 1, wherein the coupling catalyst is a catalyst comprising at least one metallic element selected from the $4^{th}$ and $5^{th}$ period of groups IIIA, IVA, VA, VIA, VIIA, VIII, IB and IIB of the periodic table.

27. A process according to claim 26, wherein the metallic element is copper, iron, cobalt, nickel, palladium or platinum.

28. A process according to claim 26, wherein the metallic element is supplied in the form of a zero metal, an oxide, an hydroxide, a mineral salt, a cyanide, an oxalate, an acetylacetonate, or an alcoholate.

29. A process according to claim 26, wherein the metallic element is supplied in the form of a nitrate, sulphate, oxysulphate, halide, oxyhalide, silicate, or carbonate.

30. A process according to claim 26, wherein the catalyst is copper metal, an organic copper I compound, an organic copper II compound, an inorganic copper I compound, or an inorganic copper II compound.

31. A process according to claim 30, the catalyst is selected from the group consisting of cuprous bromide, cupric bromide, cuprous iodide, cuprous chloride, cupric chloride, basic copper II carbonate, cuprous nitrate, cupric nitrate. cuprous sulphate, cupric sulphate, cuprous sulphite, cuprous oxide, cuprous acetate, cupric acetate, cupric trifluoromethylsulphonate, cupric hydroxide, copper I methylate. copper II methylate, and chlorocupric methylate of formula $ClCuOCH_3$.

32. A process according to claim 1, wherein the ratio between the number of moles of the disulphide compound and the number of moles of the diazonium salt is in the range from 1 to 1.5.

33. A process according to any one of claim 1, wherein the reaction of the diazonium salt of a biphenyl aromatic compound with the disulphide compound is carried out in an aqueous medium, comprising water, the quantity of water present in the medium being from 100% to 500% by weight of the biphenyl aromatic compound.

34. A process according to claim 1, characterized in wherein the reaction of the diazonium salt of a biphenyl aromatic compound with the disulphide compound is carried out in the presence of an organic solvent.

35. A process according to claim 34, wherein the solvent is acetic acid.

36. A process according to claim 1, comprising the steps of adding the disulphide compound to the diazonium salt, and then adding the catalyst.

37. A process according to claim 1, wherein the reaction of the diazonium salt of a biphenyl aromatic compound with the disulphide compound is carried out at a temperature in the range from 0° C. to 120° C.

38. A process according to claim 37, wherein the temperature is in the range from 80° C. to 100° C.

39. A process according to claim 3, wherein the biphenyl aromatic thioether compound has the following formula (VI);

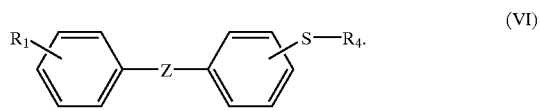

$R_1$ and Z are defined in claim 3, and $R_4$ is a hydrocarbon group having 1 to 24 carbon atoms.

40. A process according to claim 39, wherein the biphenyl aromatic thioether compound is 4-chloro-4'-thiomethyldiphenylether.

* * * * *